United States Patent
Ookubo (10) Patent No.: US 7,035,306 B2
(45) Date of Patent: Apr. 25, 2006

(54) METHOD OF ASSAYING FLUORITE SAMPLE AND METHOD OF PRODUCING FLUORITE CRYSTAL

(75) Inventor: Kenji Ookubo, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 469 days.

(21) Appl. No.: 10/187,799

(22) Filed: Jul. 3, 2002

(65) Prior Publication Data

US 2003/0027349 A1  Feb. 6, 2003

(30) Foreign Application Priority Data

Jul. 5, 2001  (JP) .............................. 2001-205469

(51) Int. Cl.
  *H01S 3/131* (2006.01)
(52) U.S. Cl. ....................................... 372/58
(58) Field of Classification Search ............... 422/68.1, 422/82.05; 372/58
See application file for complete search history.

(56) References Cited

U.S. PATENT DOCUMENTS

| | | | | |
|---|---|---|---|---|
| 4,740,982 | A * | 4/1988 | Hakuta et al. ................. | 372/59 |
| 6,028,880 | A * | 2/2000 | Carlesi et al. ................. | 372/58 |
| 6,240,117 | B1 * | 5/2001 | Gong et al. .................... | 372/58 |
| 6,804,285 | B1 * | 10/2004 | Ohmi et al. .................... | 372/58 |
| 6,878,201 | B1 * | 4/2005 | Oba et al. ...................... | 117/76 |
| 6,930,837 | B1 * | 8/2005 | Shafer et al. ............... | 359/649 |

FOREIGN PATENT DOCUMENTS

| | | |
|---|---|---|
| EP | 0 869 203 A2 | 10/1998 |
| EP | 0 995 820 A2 | 4/2000 |
| EP | 1 037 267 A1 | 9/2000 |
| JP | 2000-119097 | 4/2000 |

OTHER PUBLICATIONS

J.T. Mouchovski et al., "Growth of Ultra-Violet Grade CaF2 Crystals and Their Application for Excimer Laser Optics," 162 *J. Cryst. Growth* 79-82 (1996).
Aierken Sidike et al., "Photoluminescence Properties of a Natural Fluorite," 95 *J. Menral. Petrol. Sci.* 228-235 (2000).
European Search Report in Application No. 02254694.9 (Aug. 22, 2003).

* cited by examiner

*Primary Examiner*—Monique T. Cole
(74) *Attorney, Agent, or Firm*—Fitzpatrick, Cella, Harper & Scinto (57) ABSTRACT

Disclosed is a method of performing assay to a fluorite sample, which includes a first step for dissolving a fluorite sample, containing Ca and F, by use of a solvent, a second step for removing Ca and F from an obtained solution, and a third step for assaying, through ICP-MS, the solution having Ca and F removed therefrom. Also disclosed is a method of producing a fluorite crystal and an exposure apparatus using such fluorite crystal, and a device manufacturing method using such exposure apparatus. The assaying method of the present invention ensures assay and evaluation of a fluorite sample, of sensitivity several times higher than conventional methods.

1 Claim, 6 Drawing Sheets

METHOD OF ASSAYING FLUORITE SAMPLE AND METHOD OF PRODUCING FLUORITE CRYSTAL

FIELD OF THE INVENTION AND RELATED ART

This invention relates to a fluorite crystal to be used as an optical element in a photolithographic apparatus, which uses, for example, an excimer laser to generate exposure light, as well as to an assaying method, a production method and an optical characteristic evaluation method for such a fluorite crystal. In another aspect, the invention concerns an optical system using a fluorite crystal, an exposure apparatus using such optical system, and a device manufacturing method using such an exposure apparatus.

In order to meet recent notable advancement in miniaturization of semiconductor circuits, the wavelengths of light sources used in semiconductor exposure apparatuses have been reduced. Currently, exposure apparatuses using the $F_2$ excimer laser ($\lambda$:157 nm) are being widely developed. Under these circumstances, fluorite is expected to be an effective optical material that ensures good durability and transmissivity of short wavelengths.

However, when the fluorite contains impurities, its durability and tranamissivity will decrease. Since this effect becomes more pronounced as the wavelength of a light source becomes shorter, the impurity content is, in fact, a serious problem when fluorite is to be used as an optical material in an exposure apparatus.

In order to meet this problem, there have been attempts to improve the purity of fluorite. At present, except for congeners of Ca, such as Mg, Sr and Ba, fluorite crystals having such a purity level that no impurity can be observed in accordance with conventional assaying methods, are obtained. A typical example of a conventional assaying method is a procedure in which a fluorite sample is dissolved with acid into a solution, which is then assayed on the basis of ICP-MS/ICP-OES (Inductively Coupled Plasma-Optical Emission Spectrometry), for example. With such conventional methods, the impurity content in fluorite can be assayed quantitatively to a concentration level on the order of a few ppb.

It should be noted, however, that even such a high-purity fluorite does not assure sufficient durability and transmissivity with respect to ArF excimer lasers ($\lambda$;193 nm) or $F_2$ excimer lasers. Therefore, there still remains a problem.

Namely, fluorite crystals of a purity higher than what is obtainable currently are required. However, it is extremely difficult to meet this requirement, because most impurities in fluorite are not observed using conventional assay methods. On the one hand, a quantitative method itself for effectively reducing what is invisible is difficult to accomplish. On the other hand, contamination during the manufacturing process cannot be identified. It is not known which element is undesirable in connection with the optical characteristics, to what level such an element should be reduced and, more fundamentally, whether a further reduction of impurities has a real significance in improving optical characteristics, etc. Where impurities are at a slight trace level, on the order of a few ppb or lower, a hypothesis that a factor other than the impurities, such as the level of crystallinity, is largely responsible for the deterioration of optical characteristics may be applicable. Thus, the absence or particular guidelines fetters the development of high-quality fluorite having good optical characteristics.

SUMMARY OF THE INVENTION

In order to meet these problems, it is an object of the present invention to provide a fluorite assaying method having sensitivity several times higher than conventional methods.

It is another object of the present invention to provide fluorite which satisfies an impurity concentration range being determined idealistic to optical characteristics on the basis of the result of the assay.

It is a further object of the present invention to provide a method of producing fluorite for satisfying the allowable impurity concentration range.

It is a yet further object of the present invention to provide an optical characteristic evaluation method which is based on impurity assay for a fluorite crystal.

It is a yet further object of the present invention to provide an optical system using such fluorite crystal, a semiconductor manufacturing exposure apparatus using such optical system, and/or a device manufacturing method based on such semiconductor exposure apparatus.

Particularly, in ordinary evaluation methods for optical characteristics, a sample is polished at high precision and the characteristic of the same is measured while ArF or F2 excimer laser is projected thereto for a long period. Such evaluation method therefore needs complicated works, time and expense. Therefore, there is indeed a large problem in respect to the optical characteristic evaluation, and a simple evaluation method to be substituted for conventional methods has been desired.

In accordance with an aspect of the present invention, there is provided an assaying method for a fluorite sample, comprising: a first step for dissolving a fluorite sample, containing Ca and F, by use of a solvent; a second step for removing Ca and F from an obtained solution; and a third step for assaying, through ICP-MS, the solution having Ca and F removed therefrom.

In one preferred form of this aspect of the present invention, the first step comprises a procedure for transforming the fluorite sample into a calcium nitrate solution by use of nitric acid, and wherein the second step comprises a procedure in which the calcium nitrate solution is kept hot to remove solution, to thereby remove HF and excessive nitric acid produced in the calcium nitrate solution, in which a residual solute being dissolved into an aqueous solution is then passed through an imino diacetate-type chelating resin at an appropriate pH to separate and remove Ca, and in which an element absorbed to the imino diacetate-type chelating resin is extracted by use of nitric acid.

In accordance with another aspect of the present invention, there is provided an exposure apparatus having one of an ArF excimer laser and an F2 excimer laser as a light source, characterized in that all lens elements used in an illumination optical system and a projection optical system of said exposure apparatus and containing calcium fluoride as a major component, contain calcium fluoride as a major component and also they contain fifteen elements of Y, La, Ce, Pr, Nd, Sm, Eu, Gd, Tb, Dy, Ho, Er, Tm, Yb and Lu by weight not greater than 3 ppb, respectively.

In accordance with a further aspect of the present invention, there is provided a method of producing a fluorite crystal, comprising: a first step for fusing a fluorite raw material having a scavenger added thereto to provide a refined product; a second step for fusing and re-crystallizing the refined product to provide an ingot; a third step for annealing the obtained ingot at a temperature not greater than a melting point, thereby to improve a crystalline and to provide an annealed product; a fourth step for performing quantitative assay to at lease one of fifteen elements of Y, La, Ce, Pr, Nd, Sm, Eu, Gd, Tb, Dy, Ho, Er, Tm, Yb and Lu, in respect to at least one of the fluorite raw material, the refined product, the ingot and the annealed product; and a fifth step for controlling the first, second and third steps on the basis of the result of the assay.

The fourth step may comprise a procedure for performing quantitative assay to all the fifteen elements of Y, La, Ce, Pr, Nd, Sm, Eu, Gd, Tb, Dy, Ho, Er, Tm, Yb and Lu, in respect to at least one of the fluorite raw material, the refined product, the ingot and the annealed product.

An average weight rate of each of Y, La, Ce, Pr, Nd, Sm, Eu, Gd, Tb, Dy, Ho, Er, TM, Yb and Lu may not be greater than 100 ppb.

An average weight rate of each of Y, La, Ce, Pr, Nd, Sm, Eu, Gd, Tb, Dy, No, Er, Tm, Yb and Lu of the refined product may not be greater than 80 ppb.

An average weight rate of each of Y, La, Ce, Pr, Nd, Sm, Eu, Gd, Tb, Dy, Ho, Er, Tm, Yb and Lu of the ingot may not be greater than 50 ppb.

An average weight rate of each of Y, La, Ce, Pr, Nd, Sm, Eu, Gd, Tb, Dy, Ho, Er, Tm, Yb and Lu of the annealed product may not be greater than 50 ppb.

In accordance with a yet further aspect of the present invention, there is provided a fluorite produced in accordance with at least one of the fluorite crystal producing methods as recited above.

In accordance with a still further aspect of the present invention, there is provided an optical System for use with ultraviolet light as a light source, characterized in that a fluorite as recited above is used therein.

In accordance with a yet further aspect of the present invention, there is provided an exposure apparatus characterized in that an optical system as recited above is used therein.

In accordance with a still further aspect of the present invention, there is provided a device manufacturing method characterized in that an exposure apparatus as recited above is used in an exposure step for the device manufacture.

In accordance with another aspect of the present invention, there is provided a method of evaluating an optical characteristic of a fluorite, characterized in that quantitative assay is performed to at least one element of Y, La, Ce, Pr, Nd, Sm, Eu, Gd, Tb, Dy, Ho, Er, Tm, Yb and Lu in the fluorite.

The quantitative assay may be based on ICP-MS assay method.

The quantitative assay may be based on laser abrasion ICP-MS assay method.

In accordance with a yet further aspect of the present invention, there is provided a fluorite characterized in that at least one of the optical characteristic evaluating methods as recited above is applied.

In accordance with a still further aspect of the present invention, there is provided an optical system for use with ultraviolet light as a light source, characterized in that a fluorite as recited above is used therein.

In accordance with a yet further aspect of the present invention, there is provided an exposure apparatus characterized in that an optical system as recited above is used therein.

In accordance with a still further aspect of the present invention, there is provided a device manufacturing method characterized in that an exposure apparatus as recited above is used in an exposure step for the device manufacture.

In order to meet the problems described hereinbefore, the present invention has accomplished a sample pre-processing method which includes dissolution of a fluorite sample, removal of matrix (such as Ca, F, and solvent used for dissolution, for example), and concentration process for residual impurity elements, as well as an assay method which is characterized by use of ICP-MS (Inductively Coupled Plasma-Mass Spectrometry Apparatus). With these methods, a limit of quantitative determination of 0.1 ppb which means sensitivity hundred times higher than conventional methods can be attained. This is the highest sensitivity for fluorite, over any assay results published up to the present.

In an assay method for fluorite, as a sample pre-processing procedure, the fluorite sample may be transformed into a calcium nitrate solution by use of nitric acid, and the calcium nitrate solution may be kept hot to remove solution, to thereby remove HF and excessive nitric acid produced in the calcium nitrate solution. A residual solute being dissolved into an aqueous solution may then be passed through an imino diacetate-type chelating resin at an appropriate pH to separate, by absorption, metal elements and rare earth elements, mainly. The element absorbed to the imino diacetate-type chelating resin may be extracted by use of nitric acid. With this procedure, removal of matrix (such as Ca, F and nitric acid used for the dissolution) as well as concentration of contained impurity elements can be accomplished. This assay method is effective mainly to metal elements and rare earth elements, as a high-sensitivity assay, and a limit of quantitative determination of 0.1 ppb can be attained.

Figure 1A:
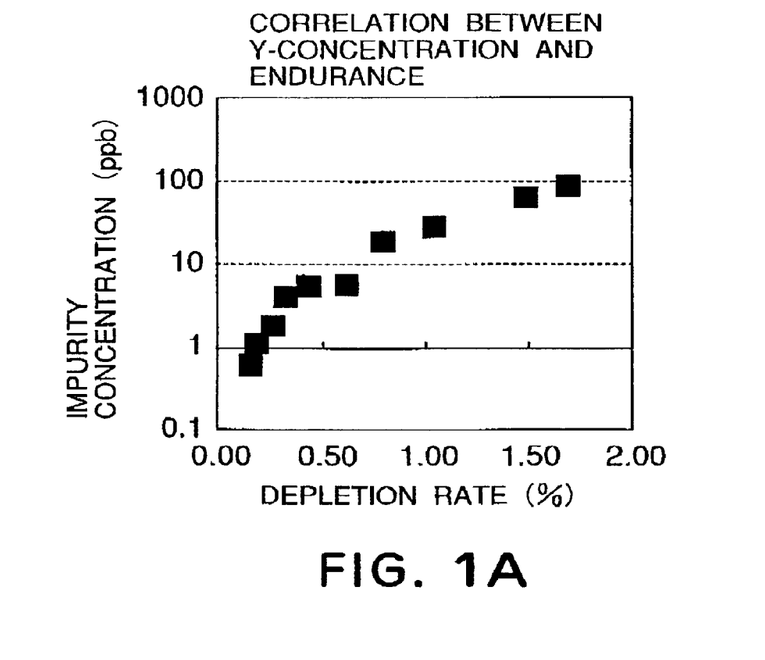
FIGS. 1A and 1B are graphs, respectively, for explaining correlations of durability and transmissivity to Y concentration in fluorite and ArF excimer laser.
Figure 1B:
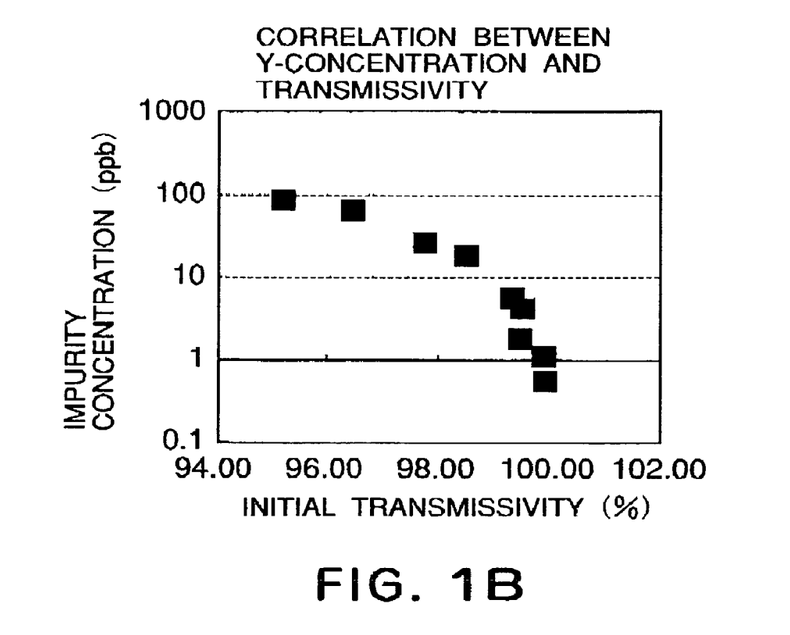

The inventor has measured content of impurities in fluorite in accordance with this newly established assay method and at a sensitivity of a quantitative determination limit of 0.1 ppb, and have investigated the correlation between the impurity content and the durability and transmissivity of fluorite, in detail. It has been confirmed experimentally that there is a correlation between rare earth elements and the optical characteristic of fluorite such as depicted in FIGS. 1A and 1B. Since the durability to F2 excimer laser corresponds approximately to that obtainable by multiplying the depletion rate (deterioration level) with respect to ArF by about 1.5, and the transmissivity corresponds to that obtainable by multiplying the value with respect to ArF by about 0.99, they are not illustrated in the drawings.

Figure 2:
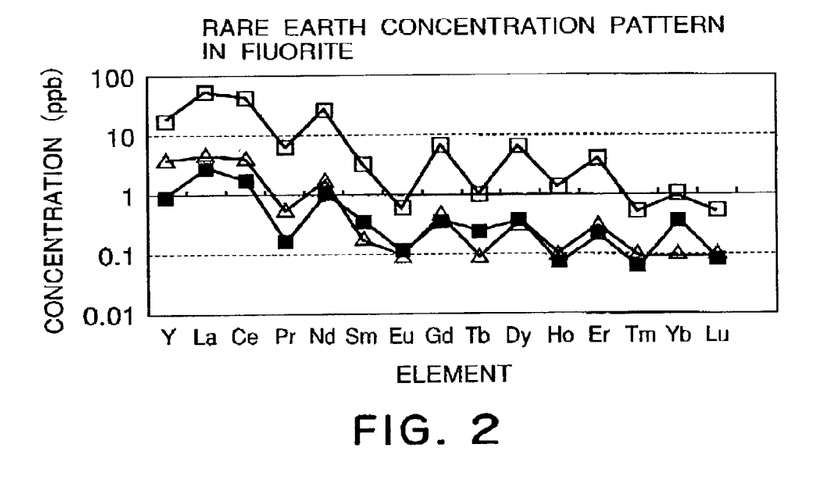
FIG. 2 is a graph for explaining a typical pattern of rare earth elements contained in fluorite.

Further, it has been confirmed that, for any fluorite sample having been assayed, there is a substantially constant rare-earth content pattern such as shown in FIG. 2.

Generally, regardless of the types of elements, if fluorite contains impurities of an amount greater than a certain threshold, a desired optical characteristic can not be satisfied. Some elements among them would have a large influence upon the optical characteristic, even if only a small amount is contained. Those which are currently regarded as a problem are, among these elements, impurities that can not be removed by all means in an existing high-purity fluorite and that may have an influence upon the optical characteristic. On the other hand, it is a pending question that whether impurities of a level of several ten ppb in fact contribute to deterioration of optical characteristic. The finding of the present invention as described above clearly indicates that the factor for deterioration of the optical characteristic of high-purity fluorite, which has not been identified, is a slight trace level of rare earth impurities, not at all the crystalline. Even the mixture pattern thereof has been specified. Indeed, these facts are epoch-making results which provide a prospect for future fluorite development. Further, the present invention does provide an impurity assaying method which is inevitable to impurity reduction. Thus, the present invention activates the fluorite development.

In the specification, the rare earth element concentration may be referred to as 50 ppb or less, for example. From this content pattern, for ordinary fluorite, this can be accomplished it Ce or the like is not greater than 50 ppb.

On the basis of the epoch-making findings as described above, the present invention provides an optical material which is suitably usable with vacuum ultraviolet light such as F2 excimer laser, and which contains calcium fluoride as a main component, wherein the content weights of rare earth elements (Y, La, Ce, Pr, Nd, Sm, Eu, Gd, Tb, Dy, Ho, Er, Tm, Yb and Lu) are not greater than 50 ppb, respectively. Here, the value "50 ppb" is the level corresponding to the durability and transmissivity that satisfy the optical characteristic standard set by us. Among them, those having a rare earth element content weight not greater than 3 ppb can show extremely good durability and transmissivity, and they can be used satisfactorily as an optical material suitable to vacuum ultraviolet light.

The present invention provides an optical system characterized by use of such an optical material described above, as an optical system suitable to vacuum ultraviolet light such as F2 excimer laser Also, the present invention provides an exposure apparatus characterized by use of such an optical system described above, as a semiconductor exposure apparatus using vacuum ultraviolet light such as F2 excimer laser.

Also, the present invention provides a device manufacturing method characterized by use of such an exposure apparatus as described above in an exposure process for device manufacture, as a semiconductor device manufacture in which micro-processing based on vacuum ultraviolet light such as F2 excimer laser is required.

Further, the present invention provides a method of producing a fluorite crystal, as a method of producing fluorite effective to obtain fluorite crystal of good optical characteristic which can be used with vacuum ultraviolet light such as F2 excimer laser, the method comprising a first step for fusing a fluorite raw material to provide a refined product, a second step for fusing and re-crystallizing the refined product to provide an ingot, a third step for annealing the obtained ingot at a temperature not greater than a melting point, thereby to improve a crystalline and to provide an annealed product. Quantitative assay to at lease one of fifteen elements of Y, La, Ce, Pr, Nd, Sm, Eu, Gd, Tb, Dy, Ho, Er, Tm, Yb and Lu, is carried out in respect to at least one of the fluorite raw material, the refined product, the ingot and the annealed product. Then, the first, second and third steps are controlled on the basis of the result of the assay.

The present invention provides a fluorite crystal producing method wherein an average weight rate of each of Y, La, Ce, Pr, Nd, Sm, Eu, Gd, Tb, Dy, Ho, Er, Tm, Yb and Lu is not greater than 100 ppb.

The present invention provides a fluorite crystal producing method wherein an average weight rate of each of Y, La, Ce, Pr, Nd, Sm, Eu, Gd, Tb, Dy, Ho, Er, Tm, Yb and Lu of the refined product is not greater than 80 ppb.

The present invention provides a fluorite crystal producing method wherein an average weight rate of each of Y, La, Ce, Pr, Nd, Sm, Eu, Gd, Tb, Dy, Ho, Er, Tm, Yb and Lu of the ingot is not greater than 50 ppb.

The present invention provides a fluorite crystal producing method wherein an average weight rate of each of Y, La, Ce, Pr, Nd, Sm, Eu, Gd, Tb, Dy, Ho, Er, TM, Yb and Lu of the annealed product is not greater than 50 ppb.

As regards the average weight rate of rare earth elements in the refined product, ingot and annealed product, a sample was collected so that the sample becomes uniform with respect to the crystal growth direction, and the average weight rate was represented by the concentration in that sample. An example is hollowing out a column-like shape along the growth direction. This is because of the tendency that the impurity increases more if solidification becomes later (recrystallization effect).

Further, the present invention provides a fluorite crystal producing method characterized by use of ICP-MS assay method as quantitative assay method, a fluorite crystal producing method characterized by use of any of the aforementioned assay method as the quantitative assay method, and a fluorite crystal producing method characterized by use of laser abrasion ICP-MS assay method.

Further, the present invention provides a fluorite as an optical material suitable to vacuum ultraviolet light such as F2 excimer laser, in which at least one of the aforementioned fluorite crystal producing methods is applied.

Further, the present invention provides an optical system, as an optical system suitable to vacuum ultraviolet light such as F2 excimer laser, in which such fluorite is used.

Further, the present invention provides an exposure apparatus, as a semiconductor exposure apparatus using vacuum ultraviolet light such as F2 excimer laser, in which such optical system is used.

Also, the present invention provides a device manufacturing method characterized by use of such an exposure apparatus as described above in an exposure process for device manufacture, as a semiconductor device manufacture in which micro-processing based on vacuum ultraviolet light such as F2 excimer laser is required.

Further, the present invention provides a method of evaluating an optical characteristic of a fluorite, characterized in that quantitative assay is performed to at least one rare earth element of Y, La, Ce, Pr, Nd, Sm, Eu, Gd, Tb, Dy, Ho, Er, Tm, Yb and Lu in the fluorite, to evaluate the durability and transmissivity of the fluorite crystal to ultraviolet light. From the content, the optical characteristic is predicted.

The present invention provides an optical characteristic evaluation method for fluorite, in which those having average weight rates of rare earth elements not greater than 50 ppb are concluded as superior fluorite crystal.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

Preferred embodiments of the present invention will be described with reference to the drawings.

Figure 3:
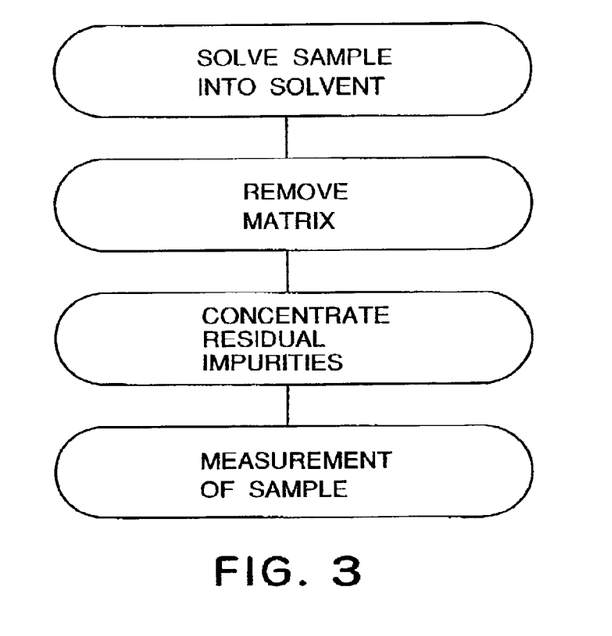
FIG. 3 is a flow chart of fluorite assaying method according to an embodiment of the present invention.

Referring now to FIG. 3, an embodiment of quantitative assay method for fluorite, having sensitivity several times higher than conventional methods, will be described. In accordance with the assay method of this embodiment, the sample preprocessing method comprises processes of dissolution of fluorite sample, removal of matrix (such as Ca, F and solvent used for the dissolution), and concentration for contained impurity elements.

First, a sample to be measured is prepared. For a solid mass, a sample of an appropriate amount can be obtained by cleavage, cutting or breaking, for example. For powder sample, we can use it as it is. After a sample is obtained, a solution is made. If however surface contamination is to be removed, before the solution making the sample surface may be removed by fusing. For example, inside a clean closed container which can be heated and which does not cause reaction, a sample may be immersed in diluted hydrochloric acid or diluted nitric acid or, alternatively, concentrated sulfuric acid and, after being closed, it may be heated. Similarly, inside a clean closed container which can be heated and which does not cause reaction, a sample may be immersed in perchloric acid and then heated. The surface can be removed by fusing, in this manner. The heating may be done to facilitate efficient fusing.

As regards the thus obtained sample, if it is a mass, it is crushed by using a milling tool such as clean agate mortar or alumina mortar. This is to expedite the fusing. Since however it may cause contamination from the mortar, the fusing process may be initiated as the mass sample is left as it is. As regards the milling tool, it may be cleaned by immersing the same in nitric acid for a long time, for example. Then, only a portion of the sample to be powdered may be crushed and abolished, and thereafter, sample crushing may be initiated. The degree of crushing should be moderate, to avoid contamination from the milling tool.

Subsequently, dissolution of the sample into solution is made. The obtained powder (or mass) sample is put into a clean container which can be heated and which does not cause reaction, and after adding a solvent for causing dissolution of fluorite, the sample is held at an appropriate temperature whereby it is fused. Examples of solvent for fusing fluorite are hydrochloric acid, nitric acid, sulfuric acid, and perchloric acid. For example, a sample may be measured in a Teflon pressure-resistant container having been washed by nitric acid, and diluted nitric acid may be added thereto. After closing the container, it may be placed in a heating oven such that the fluorite can be fused.

The next step is removal of matrix. This can be done in various ways such as separation by absorption, separation by coprecipitation, and evaporation removal of unwanted matters, for example. Now, HF evaporation removal and separation by absorption through ion exchange of impurity elements in fluorite will be described as an example. Of course, impurity elements may be separated through coprecipitation with $Fe(OH)_2$, for example.

As regards evaporation removal of HF, an obtained solution is evaporated, and product HF in the solution as well as excessive solution not reacted with fluorite are removed. For example, in the case of nitric acid solution, if it is kept heated to remove solution by means of a hot plate maintained at 200° C., HF and nitric acid are vaporized and there remains $Ca(NO_3)_2 \cdot 4H_2O$ having deliquescence.

The subsequent step is separation by absorption of impurity elements in fluorite by ion exchange. In this example, first, the residual sample is dissolved. Namely, the aforementioned $Ca(NO_3)_2 \cdot 4H_2O$ is melted by diluted nitric acid.

The thus obtained solution is passed through a clean ion exchanging resin under appropriate pH, whereby elements in question are absorbed. For example, an imino diacetate-type chelating resin refined and washed by diluted nitric acid may be put into a column. Then, and nitric acid, ammonium acetate aqueous solution and pH-adjusted sample solution may be passed through the resin in this order, whereby metal elements or rare earth ions may be absorbed to the resin. Subsequently, for washing and removing residual solution inside the column, ammonium acetate aqueous solution and ultra pure water may be passed therethrough. Finally, by using nitric acid, metal elements and rare earth ions absorbed to the resin may be extracted.

With the operations described above, matrix, that is, Ca, F and solvent used for the dissolution can be removed. Further, in this example, the amount of nitric acid for extracting impurity elements absorbed to the resin can be held relatively small, such that impurities can be concentrated much more (concentration process), as compared with fluorite solution to be conventionally introduced to ICP-MS.

With the operations described above, high-concentration fluorite solution having Ca and HF removed considerably to be suited to ICP-MS measurement can be provided. As compared with 0.1% fluorite solution which has been the upper limit to be introduced to ISP-MS because of limitation of ordinary Ca concentration, the solution now provided can accomplish a high-impurity concentration hundred times higher than the former. Also, as a result, the detection limit for impurities in fluorite is improved hundred times higher. Specifically, in the example described above, in fact a limit of quantitative determination of 0.1 ppm was accomplished.

The content of impurities in fluorite was measured in accordance with the assay method of the present invention, up to content 0.1 ppb, and the correlation between the impurity content and the durability and transmissivity of fluorite was investigated in greater detail. As a result of it, it has been experimentally confirmed that there is a correlation between rare earth elements and optical characteristic of fluorite such as depicted in FIGS. 1A and 1B.

Additionally, it has been found that, for every fluorite sample having been assayed, there is an approximately constant pattern for rare earth content such as shown in FIG. 2.

Second, an embodiment of the present invention for optical material suitable for use with vacuum ultraviolet light such as F2 excimer laser, will be described. The optical material of the present invention has a feature that it comprises a fluorite optical material which contains calcium fluoride as a major component, wherein rare earth elements which are contributable to deterioration of optical characteristic are contained by only a very small amount not influential to the optical characteristic. This is based on the epoch-making finding on the correlation between the impurity and the optical characteristic, found by the inventors.

Fluorite crystals having been produced as an optical material for vacuum ultraviolet light and having an average weight rate not greater than 50 ppb, for rare earth elements (Y, La, Ce, Pr, Nd, Sm, Eu, Gd, Tb, Dy, Ho, Er, Tm, Yb and Lu), were chosen arbitrarily, and optical characteristics of them were evaluated. All the results followed the detected correlation, and it was confirmed that required optical characteristics were satisfied.

Figure 4:
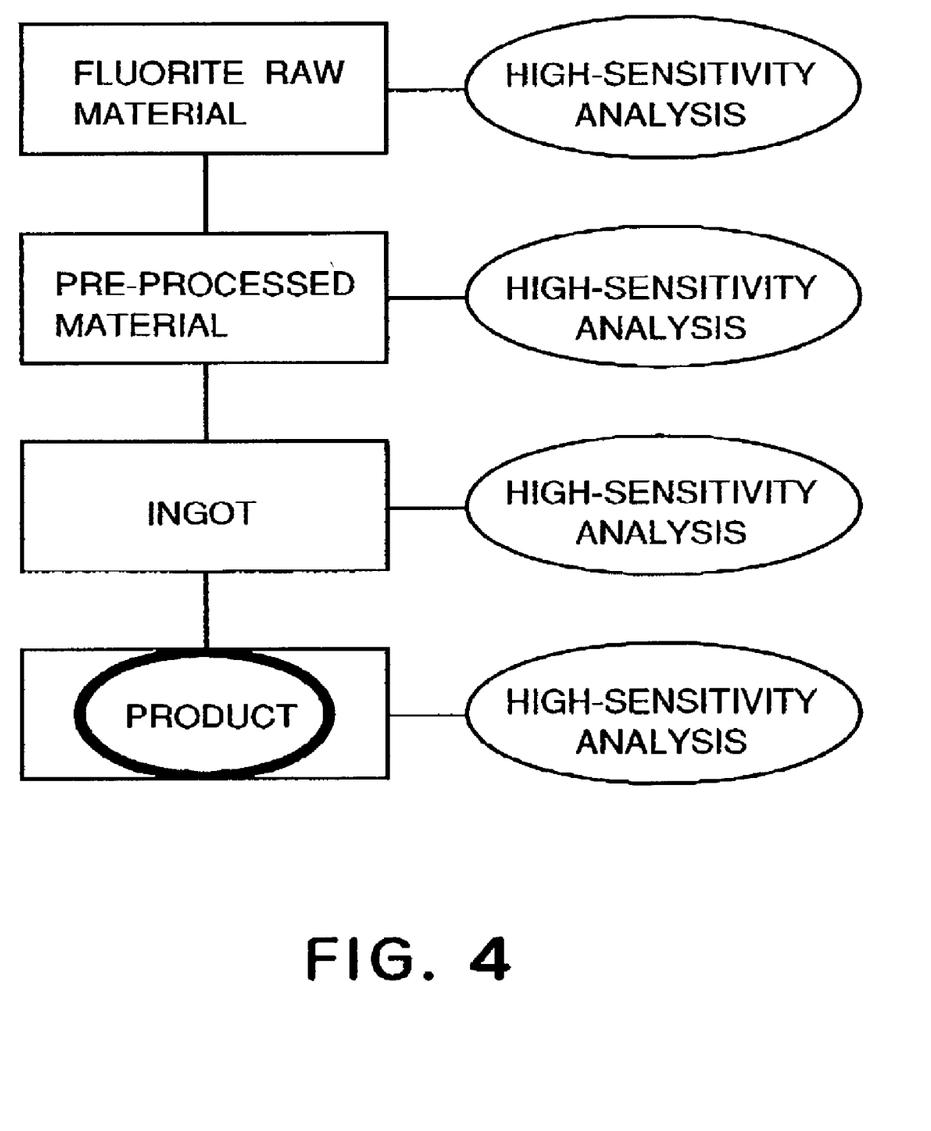
FIG. 4 is a flow chart for explaining manufacturing processes for fluorite crystal.

Third, referring to a schematic view of FIG. 4, an embodiment of a producing method for efficiently providing fluorite crystal having superior optical characteristic, will be described. The producing method according to the present invention has a feature that assay of rare earth element concentration is carried out at at least one stage in manufacturing processes, and that the process control is carried out on the basis of the result of measurement. In an example of the producing method described below, at every stage the assay was carried out.

As regards the production raw material for fluorite crystal, usually, synthetic powder raw material having less impurities is used. First, to this raw material, rare earth assay is performed in accordance with the assaying method of the present invention, for example. On the basis of this, the material is controlled so that the rare earth content included in an annealed product to be produced finally becomes small. The inventors investigated the limit quantity of contained rare earth elements, which could be accepted for fluorite raw material in practical processes, and experimentally found that the rare earth content in the fluorite raw material should desirably be not greater than 100 ppb. Here, it should be noted that, in fluorite, those portions solidified initially include less impurities, and that those portions solidified later include more impurities (recrystallization effect). Therefore, it is possible to reduce the rare earth content to some extent, in the manufacturing processes. However, if too much rare earth elements are contained in the raw material, there remains rare earth content in an annealed product, to a level that obstructs superior optical characteristics.

Subsequently, production process for refined product will be described. In this process, the fluorite raw material described above are fused and solidified, together with a scavenger. A specific example will be described below.

First, as a scavenger, 0.1 mass % of $ZnF_2$ is added to a synthetic fluorite raw material, and then they are well mixed. The obtained mixture is put into a clean container made of black lead, for example, and then it is heated in a vacuum ambience. After the mixture is fused, it is cooled slowly and solidified. Thereafter, the portion solidified later with respect to time and having more impurities contained, is removed. For example, where slow cooling is carried out in accordance with the Bridgeman method, the upper portion of the crystal may be removed.

With regard to the thus obtained refined product, rare earth assay according to the assaying method of the present invention is carried out, and the process control is performed so that an annealed product to be obtained finally includes less rare earth content. The inventors investigated the limit quantity of contained rare earth elements in the refined product, required for obtaining an annealed product having a good optical characteristic, and experimentally found through practical processes that the average rare earth content in the refined product should desirably be not greater than 80 ppb.

Next, production process of an ingot will be described. In this process, the above-described refined product is fused and solidified together with a scavenger. However, as compared with the refined product, it is cooled more slowly. This assures a good crystal having high crystalline and less grain boundary. A specific example will be described below.

As a scavenger, 0.01 mass % of $ZnF_2$ is uniformly spread over the refined product obtained as described. Then, it is put into a clean container made of black lead, for example, and it is heated in a vacuum ambience. After the mixture is fused, it is cooled and solidified by Bridgman method more slowly as compared with the refined product. Thereafter, the portion solidified later with respect to time and having more impurities contained, is removed. In this example, the upper portion of the crystal may be removed. With regard to the thus obtained ingot, rare earth assay according to the assaying method of the present invention, for example, is carried out, and the process control is performed so that an annealed product to be obtained finally includes less rare earth content. The inventors investigated the limit quantity of contained rare earth elements in the ingot, required for obtaining an annealed product having a good optical characteristic, and experimentally found through practical processes that the average rare earth content in the ingot should desirably be not greater than 50 ppb.

Finally, production process for annealed product will be described. In this process, the above-described ingot is kept at a temperature not higher than a melting point thereof and, thereafter, it is cooled slowly at a speed equivalent to or slower than that in the ingot production. Through this thermal treatment, residual stress due to distortion produced inside the ingot can be reduced, such that birefringence therein can be reduced. A specific example will be described below.

The ingot obtained as described is put into a clean container made of back lead, for example. At this time, $ZnF2$ may be added as a scavenger. As regards the ambience, a vacuum ambience or an inert gas ambience, for example, are preferable. In this state, heating is carried out at a temperature not greater than the melting point. After the ingot is held for a predetermined time period, it is cooled within a temperature range sensitive to crystal structure formation, slowly at a speed equivalent to or slower than that during the ingot production.

With regard to the thus obtained annealed product, rare earth assay according to the assaying method of the present invention, for example, is carried out, so as to directly control the rare earth content included in an annealed product to be obtained finally. The inventors investigated the limit quantity of contained rare earth elements in the annealed product, required for good optical characteristic, and experimentally found through practical processes that the average rare earth content in the annealed product should desirably be not greater than 50 ppb.

As regards the average weight rate of rare earth elements in the refined product, ingot and annealed product, a sample was collected so that the sample becomes uniform with respect to the crystal growth direction, and the average weight rate was represented by the concentration in that sample. An example is hollowing out a column-like shape along the growth direction. This is because of the tendency that the impurity increases more if solidification becomes later (recrystallization effect).

Fourth, an embodiment of a unique optical characteristic evaluation method for fluorite of the present invention, which is based on the epoch-making finding as described above, will be explained. The optical characteristic evaluation method of the present invention has a feature that, on the basis of assaying rare earth content in fluorite crystal, the optical characteristic of the crystal is predicted.

First, plural fluorite crystals having been manufactured for use with ArF or F2 excimer laser were prepared arbitrarily. Then, the average contents of rare earth elements in them were measured by use of an assay method according to the present invention. As regards the sample collection, in order that the sample become uniform with respect to the fluorite crystal growth direction, the fluorite was cut along a plane parallel to the growth direction, and an average concentration thereof was measured.

On the basis of the result of assay of rare earth concentration, the prepared fluorite crystals were classified into a group in which the rare earth content is not greater than 50 ppb and a group in which the content of at least one rare earth element is more than 50 ppb. Then, by using vacuum ultraviolet light, the durability and transmissivity were actually evaluated. The result is that, in the group in which the rare earth contents are all less than 50 ppb, the prescribed optical characteristics were cleared. In the other group in which at least one rare earth element was contained more than 50 ppb, the prescribed optical characteristics were not satisfied. It should be noted that the rare earth concentration and the optical characteristic satisfied the correlation having been found by the inventors. As described above, by measuring the rare earth concentration in fluorite crystal, the optical characteristic of fluorite can be evaluated very accurately.

Fifth, embodiments of an optical system and an exposure apparatus using fluorite, as well as a device manufacturing method using such exposure apparatus, will be described.

A fluorite produced in accordance with the present invention has good durability and high transmissivity with respect to vacuum ultraviolet light such as F2 excimer laser. For this reason, where an optical system is manufactured using such fluorite, a satisfactory optical system in which light absorption or decrease of transmissivity to ultraviolet light and which is stable in illuminance can be provided.

Further, when such optical system is incorporated into a semiconductor exposure apparatus, a semiconductor exposure apparatus in which a decrease of illuminance is very small and thus which assures good productivity, can be provided.

Further, since deterioration of imaging performance due to aberration by thermal expansion is small, use of a semiconductor exposure apparatus such as described above can provide a stable device manufacturing method.

Now, specific examples of the present invention will be described in detail

EXAMPLE 1

Example 1 relates to an assaying method for fluorite, with sensitivity several time higher then conventional methods.

First, a fluorite sample of 3 g to be impurity assayed was collected in the state of mass, by cleavage. Since the surface was contaminated, sample making was not initiated directly. By suing a Teflon beaker, the sample was immersed in perchloric acid. It was heated at about 200° C. for about 20 minutes, whereby the surface was fused and removed. The operation was carried out twice.

The mass sample having the surface fused and removed was washed by ultra pure water and, by using a Teflon evaporation plate, it was immersed in perchloric acid 15 ml. Then, on a hot plate of 180° C., it was heated until it was dried and solidified. With that procedure, product HF in the solution as well as excessive acid not reacted with fluorite were removed. To avoid contamination, it was heated in a clean booth. For similar reason, in this example, the sample powdering was not carried out.

The thus obtained material was dissolved by 3.4% diluted nitric acid. At that time, there was residual fluorite sample not melted. Thus, perchloric acid of an appropriate amount was added, and similar heating fusion and dissolution were carried out. Through these operations, finally, a diluted nitric acid solution in which a fluorite sample of 3 g was dissolved was obtained. Then, pH was adjusted by using ammonium water, to pH 6, and subsequently, it was bisected. Finally, these two solutions are made into solution of a volume 100 ml, respectively. In only one of them, rare earth elements (the subject of assay) was added by an amount corresponding to 3 ppt in terms of the concentration in solution.

The thus obtained two solutions were passed through imino diacetate-type chelating resins, respectively, at a speed of 1 ml/min, whereby metal elements and rare earth elements, etc., were separated by absorption. The chelating resin was pre-processed as follows. First, for refining, a resin of 50 ml was put into a beaker and, together with 2N nitric acid 100 ml, it was left for four or five hours while being gradually stirred. Thereafter, it was washed several times by ultra pure water. This operation was repeated once, and then, the resin of 2 ml was put into a Teflon column. Then, 2N nitric acid 8 ml, 0.1N nitric acid 8 ml and 0.2N ammonium acetate aqueous solution (pH 6) 8 ml were passed therethrough.

After the sample was passed through the resin, again, 0.2M ammonium acetate aqueous solution (pH 6) 5 ml and ultra pure water 5 ml were passed through it. Finally, 1N nitric acid 10 ml was passed, whereby rare earth elements and metal elements absorbed to the resin were extracted. Further, by using ultra pure water, the elements-extracted solution was made into a volume 20 ml. These solution making operations were carried out with respect to each of the two solutions, having been bisected. Through the procedure described, elements such as Al, V, Ni, Co, Cu, An, Ga, AG, Cd, Pb, U, Y, La, Ce, Pr, Nd, Sm, Du, Gd, Tb, Dy, Ho, Er, Tm, Yb and Lu, can be effectively separated from Ca ions.

With the operations described above, on the basis of a fluorite sample of 3 g, two high-concentration fluorite solutions (20 ml), having Ca-HF reduced considerably and being suitable for ICP-MS measurement, can be produced.

By using these two solutions, quantitative measurement based on ICP-MS was carried out. There, on the basis of information regarding the difference in concentration between the two solutions, the recovery rate for rare earth through chelating concentration was calculated. Namely, if the recovery rate is 100%, the concentration difference of solutions to be measured would be 15 ppt. If on the other hand the recovery rate is 50%, the concentration difference would be 7.5 ppt. The recovery rate for rare earth according to the procedure of this example was about 80–100%. By suing assaying method as described above, a limit of quantitative determination of 0.1 ppb was obtained, for rare earth elements, with respect to a fluorite sample.

EXAMPLE 2

Example 2 concerns an optical material suitably usable with vacuum ultraviolet light such as F2 excimer laser.

From a disk-like annealed product which was produced as a fluorite lens material for ArF stepper, a cylindrical test piece of 30 φ from an edge of the annealed product was cut. The side face of the test piece was cut, and the average rare earth concentrations in thus obtained fragments were measured. Investigations were made to ArF transmissivity and durability, to those having a rare earth concentration of not greater than 50 ppb, and the result was that all fragments showed good optical characteristics and satisfied prescribed standard. The transmissivity and durability followed the correlation with the rare earth concentration, having been found by the inventors.

EXAMPLE 3

Example 3 concerns a method of producing fluorite crystal suitably usable with vacuum ultraviolet light such as F2 excimer laser.

First, the rare earth concentration in synthetic calcium fluoride powder, i.e., the raw material of fluorite crystal, was measured in accordance with the method used in Example 1. The result was that the rare earth concentration was approximately registered with a rare earth pattern, and the Y concentration as a representative value was 67 ppb. Further, the concentrations of the other rare earth elements were not greater than 75 ppb. Thus, only raw materials having a rare earth concentration not greater than 100 ppb were selected, and they were used in the subsequent production.

Subsequently, a refined produce was produced, and the rare earth concentration of that sample was assayed in accordance with the method used in Example 1. The refined product was made as follows.

A powder of $ZnF_2$ of 0.1 mass % was added to a calcium fluoride powder material, and they were well mixed. It was put into a clean container made of black lead, and the container was put into a heating device being arranged for vacuum evacuation. While maintaining vacuum of a level about $10^{-6}$ torr inside the heating device, the container was heated up to 1450° C. After that, it was cooled by Bridgeman method to the room temperature. Then, the top surface portion where there were relatively more impurities, was removed by about 10% in volume ratio. With this procedure, a refined product (i.e. polycrystalline) was obtained.

Sampling was made so that the sample becomes uniform with respect to the crystal growth direction. As a result of assay made thereto, it was confirmed that the rare earth concentration was substantially registered with a rare earth pattern, and the Y concentration as a representative value was 53 ppb. The concentrations of the other rare earth elements were not greater than 59 ppb.

As described, only those refined products having a rare earth concentration not greater than 80 ppb were selected, and they were used in the subsequent production.

Subsequently, an ingot was produced, and the rare earth concentration of the sample was assayed in accordance with the method used in Example 1. The ingot was produced as follows.

As a scavenger, $ZnF_2$ of 0.01 mass % was sprinkled over the refined product, produced as described above. Then, it was put into a clean container made of black lead, and the container was put into a heating device being arranged for vacuum evacuation. While maintaining vacuum of a level about $10^{-6}$ torr inside the heating device, the container was heated up to 1450° C. After that, it was cooled by Bridgeman method to the room temperature. Then, the top surface portion where there were relatively more impurities, was removed by about 10% in volume ratio. With this procedure, an ingot was obtained.

Sampling was made so that the sample becomes uniform with respect to the ingot growth direction. As a result of assay made thereto, it was confirmed that the rare earth concentration was substantially registered with a rare earth pattern, and the Y concentration as a representative value was 28 ppb. The concentrations of the other rare earth elements were not greater than 32 ppb. As described, only those ingots having a rare earth concentration not greater than 50 ppb were selected, and they were used in the subsequent production.

Subsequently, an annealed product was produced, and the rare earth concentration of the sample was assayed in accordance with the method used in Example 1. The anneal product was produced as follows.

The ingot obtained as described above was processed into a predetermined shape, and the thus shaped product was put into a clean container made of black lead. Then, it was put into a heating device being arrange for vacuum evacuation. The container was heated up to 1000° C. within a vacuum of a level of about 10 torr, and it was held for 20 hours. After that, it was cooled slowly to 600° C. at a speed of 0.7° C./h. Thereafter, it was cooled to the room temperature, whereby an annealed product was obtained.

The sampling was made so that, of the annealed product, the portion to be ground in the final polishing step was cut along a plane parallel to the crystal growth direction, so as to facilitate determination of the average concentration of the annealed product. As a result of assay made thereto, it was confirmed that the rare earth concentration was substantially registered with a rare earth pattern, and the Y concentration as a representative value was 28 ppb. The concentrations of the other rare earth elements were not greater than 32 ppb. As described, only those annealed products having a rare earth concentration not greater than 50 ppb were selected as successful products, and they were used in the subsequent production.

The durability and transmissivity were actually measured to those annealed products thus obtained, and it was confirmed that they were superior fluorite crystals satisfying the prescribed standard.

EXAMPLE 4

Example 4 concerns an optical characteristic evaluation method for fluorite crystal, suitably usable with vacuum ultraviolet light such as F2 excimer laser.

First, plural fluorite crystals having been manufactured for use with ArF or F2 excimer laser were prepared arbitrarily. Then, the average contents of rare earth elements in them were measured by use of an assay method according to the present invention. As regards the measurement sample collection, the fluorite was cut along a plane parallel to the fluorite crystal growth direction, and an average concentration thereof was measured.

On the basis of the result of assay of rare earth concentration, the prepared fluorite crystals were classified into a group in which the rare earth content is not greater than 50 ppb and a group in which the content of at least one rare earth element is more than 50 ppb. That is, the former is a group of good optical characteristic, while the latter is a group not so. Then, in order to check whether the classification is valid or not, the durability and transmissivity were actually evaluated by use of vacuum ultraviolet light. The result is that, in the group in which the rare earth contents are all less than 50 ppb, the prescribed optical characteristics were cleared. In the other group in which at least one rare earth element was contained more than 50 ppb, the prescribed optical characteristics were not satisfied. It should be noted that the rare earth concentration and the optical characteristic satisfied the correlation having been found by the inventors. As described above, by measuring the rare earth concentration in fluorite crystal, the optical characteristic of fluorite can be evaluated very accurately.

EXAMPLE 5

Example 5 concerns an optical system using an optical material suitable for use with vacuum ultraviolet light such as F2 excimer laser, a semiconductor manufacturing exposure apparatus, and a device manufacturing method using such exposure apparatus.

Figure 5:
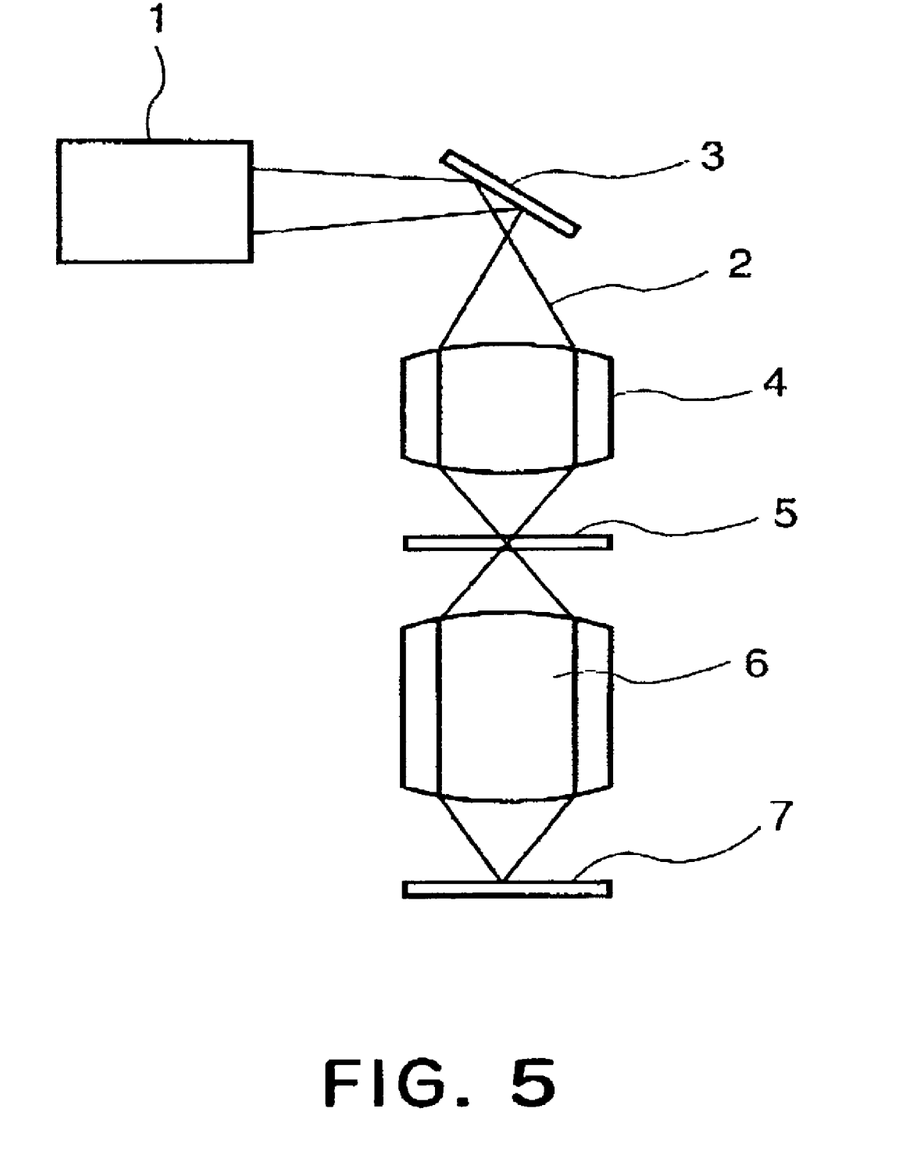
FIG. 5 is a schematic view of a semiconductor manufacturing exposure apparatus according to an embodiment of the present invention.

FIG. 5 is a schematic view of a semiconductor manufacturing exposure apparatus. Denoted at 1 in the drawing is a light source which comprises ArF excimer laser, in this example. Light beam 2 emitted from the light source 1 is directed by a mirror 3 toward an illumination optical system 4. The light beam passing through the illumination optical system 4 illuminates a reticle 5 surface (first object) The light passing through the reticle 5 and bearing information about the reticle goes through a reduction projection optical system 6, whereby it is projected on a photosensitive substrate 7.

The illumination optical system and/or the projection optical system of the semiconductor exposure apparatus of this example uses fluorite as well as quartz. The fluorite used here is one having been discriminated as a good article in Example 2, one having been manufactured in good order in Example 3, or one having been discriminated as good in Example 4.

It should be noted that, in this example, all the lenses included in the illumination optical system 4 and the reduction projection optical system 6 and being made of fluorite, contain calcium fluoride as a major component, and the weight of contained fifteen elements of Y, La, Ce, Pr, Nd, Sm, Eu, Gd, Tb, Dy, Ho, Er, Tm, Yb and Lu is not greater than 3 ppb.

A semiconductor manufacturing exposure apparatus according to Example 5 was used one year in normal operations. The illuminance on the reticle surface, after use, was measured. The result is that the illuminance was approximately at the same level as that before the apparatus was used. Further, the illuminance on the photosensitive substrate surface (wafer surface) was measured, and the result is that the illuminance was substantially at the same level as that measured before start of use of the apparatus.

As described hereinbefore, a fluorite according to the present invention has a good durability and superior transmissivity with respect to ArF excimer laser, such that, even after an exposure apparatus is used for a long term, sufficient transmissivity is assured. Additionally, aberration by thermal expansion is small. Thus, for an illumination optical system, a decrease of illuminance is small and, for a projection optical system, the imaging stability is high. In summary, an exposure apparatus which is superior in throughput and quality stability can be provided.

Next, an embodiment of a device manufacturing method which uses an exposure apparatus described above, will be explained.

Figure 6:
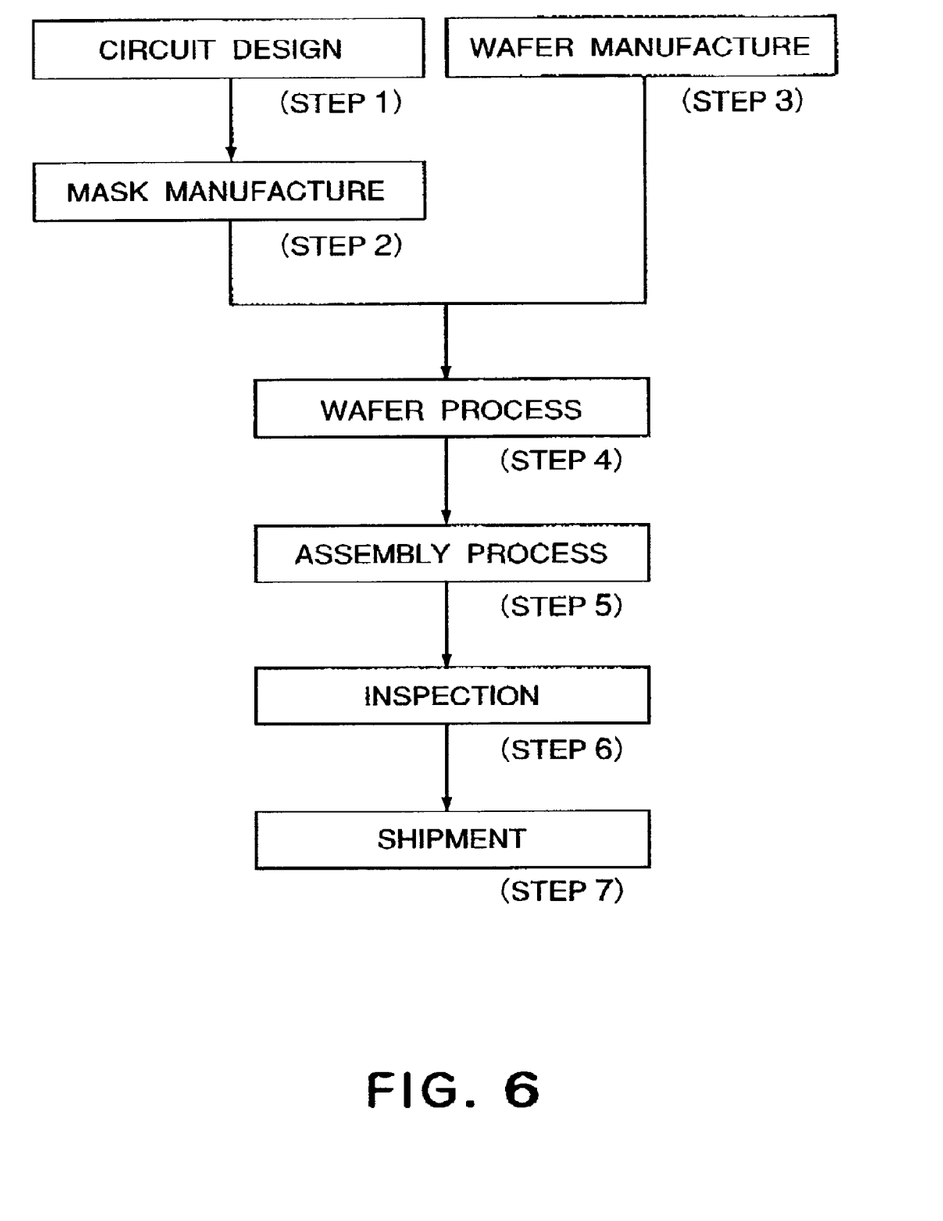
FIG. 6 is a flow chart for explaining semiconductor device manufacturing processes.

FIG. 6 is a flow chart for explaining the procedure of manufacturing various microdevices such as semiconductor chips (e.g., ICs or LSIs), liquid crystal panels, CCDS, thin film magnetic heads or micro-machines, for example. Step 1 is a design process for designing a circuit of a semiconductor device. Step 2 is a process for making a mask on the basis of the circuit pattern design. Step 3 is a process for preparing a wafer by using 4 material such as silicon. Step 4 is a wafer process in which, by using the thus prepared mask and wafer, a circuit is formed on the wafer in practice, in accordance with lithography. Step 5 subsequent to this is an assembling step wherein the wafer having been processed at step 4 is formed into semiconductor chips. This step includes an assembling (dicing and bonding) process and a packaging (chip sealing) process. Step 6 is an inspection step wherein an operation check, a durability check an so on, for the semiconductor devices produced by step 5, are carried out. With these processes, semiconductor devices are produced, and they are shipped (step 7).

Figure 7:
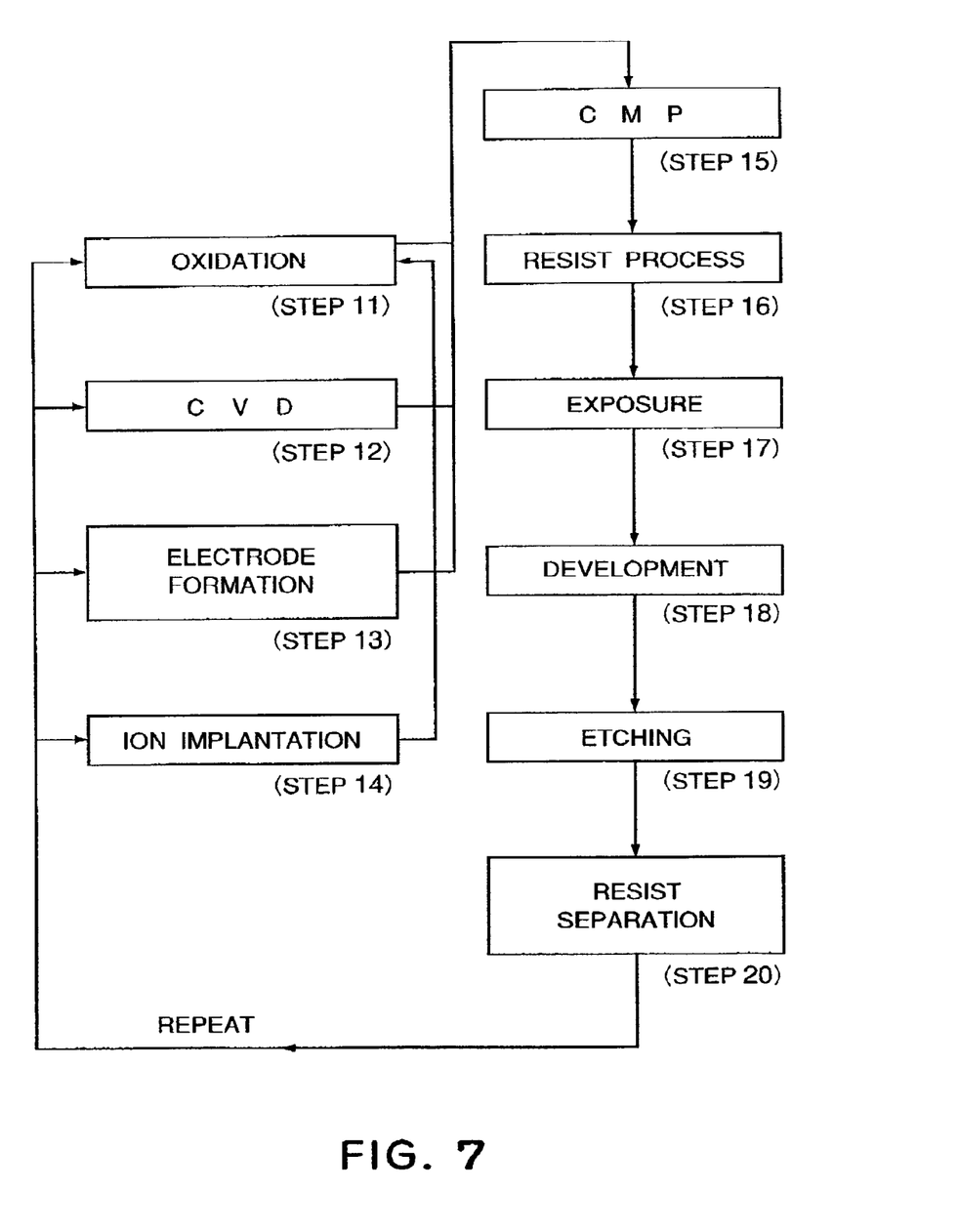
FIG. 7 is a flow chart for explaining details of a wafer process, including in the procedure of FIG. 6.

FIG. 7 is a flow chart for explaining details of the wafer process. Step 11 is an oxidation process for oxidizing the surface of a wafer. Step 12 is a CVD process for forming an insulating film on the wafer surface. Step 13 is an electrode forming process for forming electrodes upon the wafer by vapor deposition. Step 14 is an ion implanting process for implanting ions to the wafer. Step 15 is a chemical mechanical polishing step (CMP process) for polishing the wafer surface into flat, by means of a CMP device. Step 16 is a resist process for applying a resist (photosensitive material) to the wafer having been flattened. Step 17 is an exposure process for printing, by exposure, the circuit pattern of the mask on the wafer through the exposure apparatus described above. More specifically, a reticle is conveyed and it is chucked by a reticle chuck. Then, a wafer substrate having been coated with a resist is loaded into the exposure apparatus. At an alignment station, data for global alignment is read out, and on the basis of the measurement results, the wafer stage is moved so that exposures are carried out successively at predetermined positions. Step 18 is a developing process for developing the exposed wafer Step 19 is an etching process for removing portions other than the developed resist image. Step 20 is a resist separation process for separating the resist material remaining on the wafer after being subjected to the etching process. By repeating these processes, circuit patterns are superposedly formed on the wafer.

With these processes, high density microdevices can be manufactured stably and with a decreased cost.

In accordance with the present invention, impurities such as metal elements or rare earth elements which can not be detected conventionally, though they are influential to the durability or decrease of transmissivity, can be detected at a good precision. As a consequence of it, the correlation between the impurities and optical characteristics is identified, such that fluorite having good optical characteristic, a method of effectively producing such fluorite, an evaluation method for optical characteristic, for example, can be provided.

While the invention has been described with reference to the structures disclosed herein, it is not confined to the details set forth and this application is intended to cover such modifications or changes as may come within the purposes of the improvements or the scope of the following claims.

What is claimed is:

1. An exposure apparatus comprising:
a light source having an ArF excimer laser or an $F_2$ excimer laser,
an illumination optical system for illuminating a surface of a reticle with laser light emitted from the light source, the illumination optical system comprising at least one lens element; and
a projection optical system for projecting laser light, which includes information related to the reticle, onto a substrate, the projection optical system comprising at least one lens element,
wherein each lens element in both the illumination optical system and the projection optical system comprises calcium fluoride as a major component, and contains no more than 3 ppb of each of Y, La, Ce, Pr, Nd, Sm, Eu, Gd, Tb, Dy, Ho, Er, Tm, Yb and Lu.

* * * * *

UNITED STATES PATENT AND TRADEMARK OFFICE
CERTIFICATE OF CORRECTION

PATENT NO. : 7,035,306 B2
APPLICATION NO. : 10/187799
DATED : April 25, 2006
INVENTOR(S) : Kenji Ookubo It is certified that error appears in the above-identified patent and that said Letters Patent is hereby corrected as shown below:

SHEET 2

FIG. 2, "FIUORITE" should read --FLUORITE--; and
    FIG. 3, "SOLVE" should read --DISSOLVE--.

COLUMN 2

Line 9, "idealistic to" should read --to be ideal as regards--;
    Line 24, "F2" should read --$F_2$--;
    Line 52, "F2" should read --$F_2$--; and
    Line 67, "a crystalline" should read --the crystalline structure--.

COLUMN 3

Line 14, "TM," should read --Tm,--; and
    Line 30, "System" should read --system--.

COLUMN 4

Line 39, "F2" should read --$F_2$--; and
    Line 62, "crystalline." should read --crystallinity.--.

COLUMN 5

Line 10, "F2" should read --$F_2$--;
    Line 24, "F2" should read --$F_2$--;
    Line 27, "F2" should read --$F_2$--;
    Line 34, "F2" should read --$F_2$--;
    Line 39, "F2" should read --$F_2$--;
    Line 44, "a crystalline' should read --the crystallinity--; and
    Line 45, "to at lease" should read --of at least--.

COLUMN 6

Line 19, "F2" should read --$F_2$--;
    Line 23, "F2" should read --$F_2$--;
    Line 26, "F2" should read --$F_2$--; and
    Line 33, "F2" should read --$F_2$--.

UNITED STATES PATENT AND TRADEMARK OFFICE
CERTIFICATE OF CORRECTION

PATENT NO. : 7,035,306 B2
APPLICATION NO. : 10/187799
DATED : April 25, 2006
INVENTOR(S) : Kenji Ookubo It is certified that error appears in the above-identified patent and that said Letters Patent is hereby corrected as shown below:

COLUMN 7

Line 14, "concentration for" should read --determination of the concentration of--; and
Line 40, "crushed and abolished," should read --crushed,--.

COLUMN 8

Line 12, "and" should be deleted: and
Line 53, "F2" should read --$F_2$--.

COLUMN 9

Line 37, "are" should read --is--; and
Line 64, "crystalline" should read --crystallinity--.

COLUMN 10

Line 3, "Birdgman" should read --the Bridgeman--;
Line 28, "ZnF2" should read --$ZnF_2$--;
Line 30, "are" should read --is--; and
Line 64, "F2" should read --$F_2$--.

COLUMN 11

Line 27, "F2" should read --$F_2$--; and
Line 47, "time" should read --times--.

COLUMN 12

Line 3, "ammonium" should read --ammonia--;
Line 5, "solution" should read --solutions--;
Line 32, "An," should read --Au,--;
Line 33, "AG," should read --Ag,--; and "Du" should read --Eu,--;
Line 50, "suing" should read --using the--; and
Line 58, "F2" should read --$F_2$--.

UNITED STATES PATENT AND TRADEMARK OFFICE
CERTIFICATE OF CORRECTION

PATENT NO. : 7,035,306 B2
APPLICATION NO. : 10/187799
DATED : April 25, 2006
INVENTOR(S) : Kenji Ookubo It is certified that error appears in the above-identified patent and that said Letters Patent is hereby corrected as shown below:

COLUMN 13

Line 9, "F2" should read --$F_2$--;
Line 20, "produce" should read --product--; and
Line 34, "polycrystalline)" should read --a polycrystalline fluorite)--.

COLUMN 14

Line 6, "anneal" should read --annealed--;
Line 11, "arrange" should read --arranged--;
Line 13, "10 torr," should read --$10^{-6}$ torr--;
Line 31, "to" should read --of--;
Line 39, "F2" should read --$F_2$--; and
Line 41, "F2" should read --$F_2$--;
Line 60, "cleared." should read --achieved.--.

COLUMN 15

Line 3, "F2" should read --$F_2$--; and
Line 59, "using 4" should read --using a--.

UNITED STATES PATENT AND TRADEMARK OFFICE
CERTIFICATE OF CORRECTION

PATENT NO. : 7,035,306 B2
APPLICATION NO. : 10/187799
DATED : April 25, 2006
INVENTOR(S) : Kenji Ookubo

It is certified that error appears in the above-identified patent and that said Letters Patent is hereby corrected as shown below:

COLUMN 16

Line 1, "an" should read --and--;
Line 12, "into flat," should read --so that it is flat,--
Line 23, "wafer" should read --wafer.--; and
Line 46, "claims." should read --claim.--.

Signed and Sealed this

Fourteenth Day of November, 2006

JON W. DUDAS
*Director of the United States Patent and Trademark Office*